United States Patent [19]

Krespan et al.

[11] Patent Number: 5,416,246
[45] Date of Patent: May 16, 1995

[54] CHLOROFLUOROCARBON ISOMERIZATION

[75] Inventors: Carl G. Krespan; Viacheslav A. Petrov; Bruce E. Smart, all of Wilmington, Del.

[73] Assignee: E. I. Du Pont de Nemours and Company, Wilmington, Del.

[21] Appl. No.: 323,321

[22] Filed: Oct. 14, 1994

[51] Int. Cl.$^6$ .................. C07C 19/08; C07C 21/18
[52] U.S. Cl. ........................... 570/151; 570/176
[58] Field of Search ....................... 570/176, 151

[56] References Cited

U.S. PATENT DOCUMENTS

| | | | |
|---|---|---|---|
| 2,942,036 | 6/1951 | Smith et al. | 260/653 |
| 3,598,411 | 5/1952 | Miller et al. | 570/151 |
| 4,748,284 | 5/1988 | Gozzo et al. | 570/151 |
| 4,925,993 | 5/1990 | Zawalski | 570/151 |
| 5,017,732 | 5/1991 | Zawalski | 570/151 |
| 5,068,473 | 11/1991 | Kellner et al. | 570/176 |
| 5,157,171 | 10/1992 | Sievert et al. | 570/151 |
| 5,162,594 | 11/1992 | Krespan | 570/126 |

FOREIGN PATENT DOCUMENTS

| | | | |
|---|---|---|---|
| 0347830 | 12/1989 | European Pat. Off. | |
| 60-78925 | 5/1985 | Japan | |
| 5-97723 | 10/1991 | Japan | |
| 5097723 | 4/1993 | Japan | 570/151 |
| 5255141 | 10/1993 | Japan | 510/151 |

*Primary Examiner*—Alan Siegel

[57] ABSTRACT

A process is disclosed for producing a saturated gem-dichloro chlorofluorocarbon product of the formula $C_nCl_aF_b$, wherein n is 2 to 12, a is 2 to 4, and b is 4 to 24, and wherein a+b equals 2n+2 when the chlorofluorocarbon is acyclic and equals 2n when the chlorofluorocarbon is cyclic, from a starting material of the same formula which has a lesser thermodynamic stability than the saturated gem-dichloro chlorofluorocarbon product. The process involves isomerizing the starting material in the presence of (1) a catalyst of the formula $AlZ_3$, where Z is selected from F, Cl and/or Br (provided that $AlZ_3$ cannot be entirely $AlF_3$) and (2) an effective amount of promoter selected from the group consisting of is selected from hexafluoropropene, 2-chloropentafluoropropene, perfluorobutenes, perfluoropentenes, perfluorocyclobutene, 1-chlorocyclobutene, 1,2-dichlorocyclobutene, perfluorocyclopentene, 1-chlorocyclopentene, and 1,2-dichlorocyclopentene, and mixtures thereof, to accelerate production of the saturated gem-dichloro chlorofluorocarbon product. Also disclosed is a process for producing a halohydrocarbon of the formula $C_nH_cCl_dF_b$ from a gem-dichloro product produced by said isomerization (where c is 1 to 4 and c+equals a) which involves hydrodechlorinating the gem-dichloro product.

9 Claims, No Drawings

CHLOROFLUOROCARBON ISOMERIZATION

FIELD OF THE INVENTION

The invention relates to isomerizing saturated chlorofluorocarbons having lesser thermodynamic stability to saturated chlorofluorocarbons having greater thermodynamic stability, and to the use of such isomerization in halohydrocarbon production.

BACKGROUND OF THE INVENTION

Chlorofluorocarbons (i.e., CFCs ) are compounds containing carbon, fluorine and chlorine. Various CFCs have been used for many years as refrigerants, heat transfer media, foam expansion agents, aerosol propellants, solvents and power cycle working fluids. However, there has been recent concern that chlorofluorocarbons such as $CCl_2F_2$ (i.e., CFC-12) and $CCl_3F$ (i.e., CFC-11) might be detrimental to the Earth's ozone layer. Consequently, there is a worldwide effort to find alternative compounds which contain fewer chlorine substituents, preferably compounds containing no chlorine. The industry has focused on the use of perfluorocarbons, tetrafluoroethanes and hydrochlorofluorocarbons in recent years, since these compounds are believed not to contribute significantly to ozone depletion. Of particular interest to the refrigerant industry is 1,1,1,2-tetrafluoroethane (HFC-134a) . This compound can be derived from the intermediates 1,1-difluorotetrachloroethane (CFC-112a), 1,1,1-trifluorotrichloroethane (CFC-113a) and 1,2,2,2-tetrafluorodichloroethane (CFC-114a) . These intermediates are, in turn, the isomers of the more readily available chlorofluoroethanes 1,1,2,2-tetrachloro-1,2-difluoroethane (CFC-112), 1,2,2-trichloro-1,1,2-trifluoroethane (CFC-113) and 1,2-dichloro1,1,2,2-tetrafluoroethane (CFC-114), respectively.

The isomerization of such chlorofluoroethanes by treatment with aluminum trichloride is well documented in the art. For example, U.S. Pat. No. 5,017,732 discloses a process for isomerizing CFC-113 or CFC-114 to CFC-113a or CFC-114a, respectively, by contacting CFC-113 or CFC-114 with an activated aluminum trichloride catalyst. The catalyst is prepared by contacting the chlorofluorocarbon with anhydrous aluminum trichloride in the presence of a selected metal.

Another hydrofluorocarbon of interest is 1,1,1,3,3,3-hexafluoropropane (i.e., $CF_3CH_2CF_3$ or HFC-236fa). HFC-236fa can be prepared by the hydrodechlorination of 2,2-dichlorohexafluoropropane (CFC-216aa) over a rhenium containing catalyst (U.S. Pat. No. 5,068,473). The preparation of CFC-216aa by the rearrangement of 1,2-dichlorohexafluoropropane using fluorinated alumina catalysts has been disclosed (Japanese Patent Application No. 60-78925).

HFC-236fa is useful as a refrigerant, fire extinguishant, heat transfer medium, gaseous dielectric, sterilant carrier, polymerization medium, particulate removal fluid, carrier fluid, buffing abrasive agent, displacement drying agent and power cycle working fluid.

There is interest in developing more efficient methods for obtaining isomerized products of polychlorofluorocarbons containing lesser, preferably, negligible amounts of non-isomerized starting materials. These polychlorofluorocarbons can be used to prepare useful hydrofluorocarbons (HFCs) by hydrodechlorination processes.

SUMMARY OF THE INVENTION

This invention provides a process for producing a saturated gem-dichloro chlorofluorocarbon product of the formula $C_nCl_aF_b$, wherein n is an integer from 2 to 12, a is an integer from 2 to 4, and b is an integer from 4 to 24, and wherein a+b equals 2n+2 when the chlorofluorocarbon is acyclic and equals 2n when the chlorofluorocarbon is cyclic, from a starting material of the same formula which has a lesser thermodynamic stability than said saturated gem-dichloro chlorofluorocarbon product. The process comprises isomerizing said starting material in the presence of (1) a catalyst of the formula $AlZ_3$, where Z is selected from the group consisting of F, Cl, Br, and mixtures thereof, provided that the $AlZ_3$ is not entirely $AlF_3$ and (2) an effective amount of promoter selected from the group consisting of hexafluoropropene, 2-chloropentafluoropropene, perfluorobutenes, perfluoropentenes, perfluorocyclobutene, 1-chlorocyclobutene, 1,2-dichlorocyclobutene, perfluorocyclopentene, 1-chlorocyclopentene, and 1,2-dichlorocyclopentene, and mixtures thereof, to accelerate production of said saturated gem-dichloro chlorofluorocarbon product.

This invention further provides a process for producing a halohydrocarbon of the formula $C_nH_cClF_b$ from a gem-dichloro product produced by said isomerization where n and b are as defined above for said gem-dichloro product, c is an integer from 1 to 4 and the sum c+d equals a (where a is as defined above for said gem-dichloro product) comprising hydrodechlorinating said gem-dichloro product.

DETAILED DESCRIPTION

The chlorofluorocarbon starting materials of this invention can be prepared by conventional methods (e.g., chlorine addition to perfluoroolefins). The isomerization process of this invention allows isomerizing chlorofluorocarbon starting materials which contain at least two vicinal, geminal or distal halogen atoms or mixtures thereof with the catalyst as defined herein. Halogen atoms on adjacent carbon atoms are designated vicinal (e.g., $CF_3CClFCClFCF_2CF_3$). Halogen atoms on the same carbon atom are designated geminal (e.g., $C_2F_5CCl_2C_2F_5$). Halogen atoms that are separated by one or more carbon atoms are designated distal (e.g., $CClF_2CF_2CClF_2$). Examples of suitable starting materials include $CClF_2CClF_2$ and $CClF_2CClFCF_3$. Of note are isomerizations where the compound isomerized has a 4-membered carbon ring or a 5-membered carbon ring.

The catalyst used is of the structure $AlZ_3$, where Z is one or more of F, Cl or Br, provided that Z cannot be entirely F. Of note are catalysts which have the formula $AlCl_xF_y$ (mixed aluminum halide), where the total number of atoms of halide (i.e., x plus y) equals 3, where x is from about 0.05 to 2.95 and y is from about 2.95 to 0.05. Preferred catalysts include those where y is from about 2.5 to 2.95. Details of aluminum chlorofluoride catalyst preparation are disclosed in U.S. Pat. No. 5,162,594.

The promoter is one or more compounds selected from hexafluoropropene, 2-chloropentafluoropropene, perfluorobutenes, perfluoropentenes, perfluorocyclobutene, 1-chlorocyclobutene, 1,2-dichlorocyclobutene, perfluorocyclopentene, 1-chlorocyclopentene, and 1,2-dichlorocyclopentene.

Reaction temperatures typically range from about 20° C. to about 200° C. depending on the reactivity of the reagents, and are preferably in the range of about 50° C. to about 150° C. Pressures are typically from about 0.5 atm to about 200 atm, and more preferably from about 1 atm to about 100 atm. The reaction contact times are typically from about 2 minutes to about 24 hours. Reaction contact times vary depending upon the identity of the reactants, the temperature, pressure and amount of catalyst. Generally, the greater the temperature, pressure and the catalyst amount, the shorter the contact time.

The reaction may advantageously be conducted in a liquid phase and can be performed in several modes, for example, batchwise, with addition of reactant, catalyst and promoter to a reactor cold and warming of these materials to reaction temperature; semi-batch by injection of the reactant (optionally together with catalyst and/or promoter) into a vessel containing catalyst and/or promoter; or continuously by passing the reactant (typically at least partly liquified) optionally together with catalyst and/or promoter through a reaction zone which also optionally contains catalyst and/or promoter. The catalyst must be present in the reactant mixture or the reaction zone but may be present in both places. The promoter can be recovered and is available for recycle. Vapor phase isomerizations are also contemplated within the scope of this invention.

In a batch reaction, the catalyst is typically from about 0.05% to about 20% by weight of the initial chlorofluorocarbon starting material, and is preferably from about 1% to about 5% by weight thereof. The molar ratio of the promoter to the initial chlorofluorocarbon starting material is typically from about 1:50 to about 1:1000, and preferably from about 1:100 to about 1:500.

The geminal dichloro isomers produced by the isomerizations of this invention process are useful as intermediates in the production of halohydrocarbons of the formula $C_nH_cCl_dF_b$, wherein n and b are as defined above, and c+d equals a, where c is an integer from 1 to 4 and a is as defined above, by hydrodechlorination. Hydrodechlorination of the geminal dichloro isomers may be accomplished using conventional processes, for example, as disclosed in U.S. Pat. No. 2,942,036, C. Gervasutti et al., J. Fluorine Chem., 19, 1–20 (1981) and European Patent Publication No. 0 347 830.

Practice of the invention will become further apparent from the following non-limiting examples.

EXAMPLE 1

$CClF_2CClFCF_3 \rightarrow CF_3CCl_2CF_3$

Aluminum chlorofluoride (ACF) (0.75 g) and 1,2-dichlorohexafluoropropane (50 mmol), prepared by chlorine addition to hexafluoropropene, were loaded inside a dry box into a 20-mL heavy wall glass sample tube, equipped with a Teflon ® polytetrafluoroethylene (PTFE) stopcock. The reactor was cooled in liquid nitrogen, evacuated, and hexafluoropropene (3 mmol) was condensed into the sample tube reactor. The reactor was warmed to room temperature, heated to and maintained at 130° C. According to IR and $^{19}F$ NMR analyses, after 5 h the reaction was completed. The conversion of the starting material was 100%. The yield of 2,2-dichlorohexafluoropropane according to $^{19}F$ NMR was quantitative. Data on the isomerization of 1,2-dichlorohexafluoropropane are summarized in Table 1. Runs 1, 3, 6–10, 12, 13 and 15 are of this invention. Runs 2, 4, 5, 12, 17 and 19 are for comparison. The comparative runs show that in the absence of HFP or CPFP promoter, aluminum chlorofluoride is a reagent and not a catalyst.

TABLE 1

Isomerization of 1,2-Dichlorohexafluoropropane (i.e., 1,2-DHFP) at 130° C.

| Run No. | ACF (g) | Promoter (mmol) | Time (h) | Conversion* of 1,2-DHFP (%) |
|---|---|---|---|---|
| 1 | 0.25 | HFP (3) | 5 | 44 |
| 2 | 0.25 | None | 5 | 1 |
| 3 | 0.5 | HFP (3) | 4 | 67 |
| 4 | 0.5 | None | 4 | 0 |
|   |      |      | 23 | 75 |
| 5 | 0.75 | None | 5 | 26 |
| 6 | 0.75 | HFP (1.5) | 4 | 98 |
| 7 | 0.75 | HFP (6) | 4 | 90 |
| 8 | 0.75 | CPFP (1.5) | 5 | 84.1 |
| 9 | 0.5 | PFCB (3) | 4 | 76.8 |
| 10 | 0.5 | PFCP (3) | 4 | 51.2 |
| 11 | 0.5 | PFCH (3) | 4 | 16.8 |
| 12 | 0.5 | none | 4 | 11.8 |
| 13 | 1.0 | HFP (3) | 5 | 93 |
| 14 | 1.0 | None | 5 | 48 |
| 15 | 1.0 | CPFP (3) | 5 | 100 |
| 16 | 1.25 | HFP (3) | 4 | 100 |
| 17 | 1.25 | None | 4 | 47.8 |
|    |      |      | 23 | 75 |
| 18 | 1.5 | HFP (3) | 7 | 100 |
| 19 | 1.5 | None | 5 | 87 |
|    |      |      | 23 | 88 |

*Based on IR (gas-phase) and $^{19}F$ NMR data
HFP is hexafluoropropene; CPFP is 2-chloropentafluoro propene; PFCB is perfluorocyclobutene; PFCP is perfluorocyclopentene; PFCH is perfluorocyclohexene

EXAMPLE 2

$CClF_2CClFCF_2 \rightarrow CF_3CCl_2CF_3$

The procedure of Runs 3 and 4 of Table 1 was followed, except that the reaction time was 5 hours and the temperature was 50° C. Data on the isomerizations are summarized in Table 2.

TABLE 2

Isomerization of 1,2-Dichlorohexafluoropropane (i.e., 1,2-DHFP) at 50° C.

| Run No. | ACF (g) | Promoter (mmol) | Time (h) | Conversion of 1,2-DHFP (%) |
|---|---|---|---|---|
| 20 | 0.5 | HFP (3) | 5 | 22 |
| 21 | 0.5 | None | 5 | 0.2 |

EXAMPLE 3

$CClF_2CClF_2 \rightarrow CCl_2FCF_3$

As in Example 1, a mixture of ACF (1 g), 1,2-dichlorotetrafluoroethane (30 mmol, 88% of 1,2- and 12% of 1,1-dichlorotetrafluoroethane), cyclic dimer of hexafluoropropene (5 mL, present as solvent) and hexafluoropropene (HFP; 3 mmol) was kept at 100° C. After 15 h at this temperature according to $^{19}F$ NMR, the reaction mixture contained: 1.9% of $C_2F_5Cl$, 22% of 1,2-dichlorotetrafluoroethane, 75% of 1,1-dichlorotetrafluoroethane and 1.1% of $CF_3CCl_3$. Conversion of 1,2-dichlorotetrafluoroethane was 78%, yield of the product based on converted CFC-114 was 96%.

In a control experiment (the same scale and conditions, but without HFP) after 15 h at 100° C., the reaction mixture contained: 12% $C_2F_5Cl$, 48.4% $CF_3CCl_2F$, 2.8% $CF_2ClCF_2Cl$, and 37% $CF_3CCl_3$. Conversion of $CF_2ClCF_2Cl$ was 97%, and the yield of $CF_3CCl_2F$ based on converted starting material was only 50% due to the formation of by-products of disproportionation.

EXAMPLE 4

CF$_3$CFClCFClCF$_3$→CF$_3$CCl$_2$CF$_2$CF$_3$

Two 25 mL Pyrex® sample tubes, equipped with Teflon® PTFE stopcocks, were loaded inside a drybox with 1 g of ACF, 6.5 g (24 mmol) of CF$_3$CFClCFClCF$_3$ (mixture of 56% CF$_3$CFClCFClCF$_3$ and 44% of CF$_3$CCl$_2$CF$_2$CF$_3$). Both sample tubes were evacuated at −196° C. and 3 mmol of HFP were condensed through a vacuum line into one of the sample tubes. Both tubes were kept at 130° C. The conversion of CF$_3$CFClCFCl$_3$ was checked from time to time in both reactors by GC and $^{19}$F NMR. After 5 h, conversion in the sample tube with HFP was 95.5%; in the control experiment it was 28%; after 18 h the conversions were 100% and 80%, respectively. CF$_3$CCl$_2$CF$_2$CF$_3$ was identified by comparision of NMR and GC data with an authentic sample.

EXAMPLE 5

CF$_3$CClFCClFCF$_2$CF$_3$→CF$_3$CCl$_2$(CF$_2$)$_2$CF$_3$+C$_2$F$_5$-CCl$_2$C$_2$F$_5$

The procedure of Example 4 was followed using 8 g (25 mmol) of 2,3-dichloroperfluoropentane (94% purity, the rest was perfluoropentene-2), 1 g of ACF and 3 mmol of HFP. After 2 h at 130° C. the sample according to $^{19}$F NMR contained 3.5% HFP, 4.5% of perfluoropentene-2, 43.5% CF$_3$CCl$_2$C$_3$F$_7$, 16% (C$_2$F$_5$)$_2$CCl$_2$ and 32% of starting material.

In a control experiment (without HFP) the ratio was perfluoropentene-2, 4%; CF$_3$CCl$_2$C$_3$F$_7$, 65.5%; (C$_2$F$_5$)$_2$CCl$_2$, 18.5%; and starting material, 12.5%.

After 14 h the reaction mixture contained 85% of CF$_3$CCl$_2$CF$_2$CF$_2$CF$_3$ and 15% of (C$_2$F$_5$)$_2$ CCl$_2$; in a control experiment (without HFP) the ratio of these two was 93:7.

$^{19}$F NMR CF$_3^A$CCl$_2$CF$_2^C$CF$_2^D$CF$_3^B$: A −74.28 (3F, m), B −81.35 (3F, t), C −110.69 (2F, m), D −121.83 (2F, m) ppm, J$_{A-C}$ was 7, J$_{B-C}$ was 11 Hz. (CF$_3^A$CF$_2^B$)$_2$ CCl$_2$A −76.58 (3F, t), −113.01 (2F, q) ppm, J$_{A-B}$ was 4 Hz. The standard was CCl$_3$F.

This example shows that perfluoropentene-2 can also be used as a promoter.

EXAMPLE 6

C$_2$F$_5$CCl$_2$C$_2$F$_5$→CF$_3$CCl$_2$(CF$_2$)$_2$CF$_3$

The procedure of Example 4 was followed using 5 g of a mixture 2,2- and 3,3-dichloroperfluoropentane (85:15), 0.5 g of ACF and i mmol HFP. After 14 h at 130° C. the ratio, according to $^{19}$F NMR was 95:5.

EXAMPLE 7

The procedure of Example 4 was followed using two sample tubes loaded each with 6 g (26 mmol) of 1,2-dichloroperfluorocyclobutane (mixture of trans and cis isomers in ratio 53.5:46.5) and 1 g of ACF. Both tubes were evacuated at −196° C. and 3 mmol of HFP were loaded into one of them. Both tubes (experiment and control) were kept at 130° C. After 45 h, according to $^{19}$F NMR the crude reaction mixture contained 16.5% of the trans isomer, 47.5% of the cis isomer and 36.5% of 1,1-dichlorocyclobutane, conversion of the trans isomer was 69%.

In the control sample the ratio of these three was 30.3%, 48.5% and 20%, conversion of the trans isomer was 43%. After 70 h the ratio of these three compounds in the reaction mixture was 13.5, 45.9 and 40.5%, conversion of the trans isomer was 75%. In the control experiment the ratio was 22.3, 47.7 and 29.5% respectively; conversion of the trans isomer was 55%.

$^{19}$F NMR of 1,1-dichloroperfluorocyclobutane: −120.42 (4F, m), −127.40 (2F, m).

EXAMPLE 8

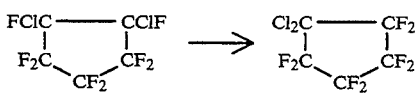

The procedure of Example 5 was followed using 7 g (25 mmol) of 1,2-dichloroperfluorocyclopentane (mixture of trans and cis isomers 74:26), 1 g of ACF and 3 mmol of HFP at 130° C. After 2 h according to $^{19}$F NMR, the reaction mixture contained 47% of trans 1,2-dichloroperfluorocyclopentane and 53% of 1,1-dichloroperfluorocyclopentane, accounting for 96% of the sample (GC). Conversion of the cis isomer was 100%, and of the trans isomer, 36.5%.

In a control experiment (without HFP), after 2 h the product contained 43% trans and 2% cis isomers of 1,2-dichloroperfluorocyclopentane and 55% of 1,1-dichloroperfluorocyclopentane. Conversion of the cis isomer was 92% and of the trans isomer, 42%. Selectivity in both cases was over 95%.

$^{19}$F NMR of 1,1-dichloroperfluorocyclopentane: −119.34 (4F, s), −123.84 (4F, s).

What is claimed is:

1. A process for producing a saturated gem-dichloro chlorofluorocarbon product of the formula C$_n$Cl$_a$F$_b$, wherein n is an integer from 2 to 12, a is an integer from 2 to 4 and b is an integer from 4 to 24, and wherein a+b equals 2n+2 when the chlorofluorocarbon is acyclic and equals 2n when the chlorofluorocarbon is cyclic, from a starting material of the same formula which has a lesser thermodynamic stability than said gem-dichloro chlorofluorocarbon product, comprising:

isomerizing said starting material in the presence of (1) a catalyst of the formula AlZ$_3$, where Z is selected from the group consisting of F, Cl, Br and mixtures thereof, provided that the AlZ$_3$ is not entirely Al$_3$, and (2) an effective amount of promoter selected from the group consisting of hexafluoropropene, 2-chloropentafluoropropene, perfluorobutenes, perfluoropentenes, perfluorocyclobutene, 1-chlorocyclobutene, 1,2-dichlorocyclobutene, perfluorocyclopentene, 1-chlorocyclopentene, and 1,2-dichlorocyclopentene, and mixtures thereof, to accelerate production of said saturated gem-dichloro chlorofluorocarbon product.

2. The process of claim 1 wherein the compound isomerized is selected from CClF$_2$CClF$_2$ and CClF$_2$CClFCF$_3$.

3. The process of claim 1 wherein the compound isomerized has a 4-membered carbon ring or a 5-membered carbon ring.

4. The process of claim 1 wherein the promoter is perfluoropentene.

5. The process of claim 1 wherein the promoter is hexafluoropropene.

6. The process of claim 1 wherein the promoter is perfluorocyclobutene.

7. The process of claim 1 wherein the catalyst has the formula $AlCl_xF_y$ wherein $x+y$ equals 3, and wherein x is from about 0.05 to 2.95.

8. The process of claim 7 wherein y is from about 2.5 to 2.95.

9. A process for producing a halohydrocarbon of the formula $C_nH_cCl_dF_b$ from a saturated gem-dichloro chlorofluorocarbon product of the formula $C_nCl_aF_b$, wherein n is an integer from 2 to 12, a is an integer from 2 to 4, b is an integer from 4 to 24, c is an integer from 1 to 4, c+d equals a, and a+b equals 2n+2 when the chlorofluorocarbon is acyclic and equals 2n when the chlorofluorocarbon is cyclic, comprising:

producing said gem-dichloro chlorofluorocarbon product by isomerizing a starting material of the same formula as said gem-dichloro chlorofluorocarbon product which has a lesser thermodynamic stability than said gem-dichloro product in the presence of (1) a catalyst of the formula $AlZ_3$, where Z is selected from the group consisting of F, Cl, Br and mixtures thereof, provided that $AlZ_3$ is not entirely $AlF_3$; and (2) an effective amount of promoter selected from the group consisting of is selected from hexafluoropropene, 2-chloropentafluoropropene, perfluorobutenes, perfluoropentenes, perfluorocyclobutene, 1-chlorocyclobutene, 1,2-dichlorocyclobutene, perfluorocyclopentene, 1-chlorocyclopentene, and 1,2-dichlorocyclopentene, and mixtures thereof, to accelerate production of said gem-dichloro product; and hydrodechlorinating said gem-dichloro product.

* * * * *